United States Patent
Ohsawa et al.

(10) Patent No.: US 9,067,972 B2
(45) Date of Patent: Jun. 30, 2015

(54) SKIN AGING-INHIBITING PEPTIDE

(75) Inventors: Kazuhito Ohsawa, Sagamihara (JP);
Naoto Uchida, Sagamihara (JP);
Hidehiko Baba, Sagamihara (JP);
Michio Hatori, Tokyo (JP); Kohji Ohki,
Sagamihara (JP)

(73) Assignee: CALPIS CO., LTD., Tokyo (JP)

( * ) Notice: Subject to any disclaimer, the term of this patent is extended or adjusted under 35 U.S.C. 154(b) by 592 days.

(21) Appl. No.: 12/874,610

(22) Filed: Sep. 2, 2010

(65) Prior Publication Data

US 2011/0092431 A1   Apr. 21, 2011

Related U.S. Application Data

(63) Continuation of application No. PCT/JP2009/070912, filed on Dec. 15, 2009.

(30) Foreign Application Priority Data

Dec. 15, 2008 (JP) ................................ 2008-318334

(51) Int. Cl.
| | |
|---|---|
| A61K 38/07 | (2006.01) |
| C07K 16/00 | (2006.01) |
| C07K 5/103 | (2006.01) |
| C07K 5/083 | (2006.01) |
| C07K 5/107 | (2006.01) |
| C07K 7/06 | (2006.01) |
| A61K 38/00 | (2006.01) |

(52) U.S. Cl.
CPC .................. *C07K 5/101* (2013.01); *A61K 38/00* (2013.01); *C07K 5/0808* (2013.01); *C07K 5/1016* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 5,449,661 A | 9/1995 | Nakamura et al. | |
| 6,994,987 B1* | 2/2006 | Yamamoto et al. | 435/68.1 |
| 7,579,315 B2 | 8/2009 | Smith | |
| 2005/0085422 A1 | 4/2005 | Georgiades | |
| 2006/0019884 A1 | 1/2006 | Smith | |
| 2006/0089493 A1* | 4/2006 | McLachlan et al. | 536/23.5 |
| 2007/0122454 A1 | 5/2007 | Yoshimura et al. | |
| 2007/0160558 A1 | 7/2007 | Smith | |
| 2008/0063674 A1 | 3/2008 | Vollhardt et al. | |
| 2008/0085299 A1 | 4/2008 | Georgiades | |
| 2009/0209728 A1 | 8/2009 | Honma et al. | |
| 2009/0325885 A1 | 12/2009 | Miyata et al. | |
| 2010/0151039 A1 | 6/2010 | Yoshimura et al. | |
| 2010/0166877 A1 | 7/2010 | Baba et al. | |

FOREIGN PATENT DOCUMENTS

| | | |
|---|---|---|
| CN | 1090201 A | 8/1994 |
| CN | 1423704 A | 6/2003 |
| JP | 6-40944 A | 2/1994 |
| JP | 2001-136995 A | 5/2001 |
| JP | 2001-224334 A | 8/2001 |
| JP | 2002-255847 A | 9/2002 |
| JP | 2002-284668 A | 10/2002 |
| JP | 2003-137807 A | 5/2003 |
| JP | 2004-115438 A | 4/2004 |
| JP | 2004-331564 A | 11/2004 |
| JP | 2004-331565 A | 11/2004 |
| JP | 2004-331566 A | 11/2004 |
| JP | 2005-29486 A | 2/2005 |
| JP | 2005-206578 A | 8/2005 |
| JP | 2006-143671 A | 6/2006 |
| JP | 2007-91637 A | 4/2007 |
| JP | 2007-145795 A | 6/2007 |
| JP | 2007-145845 A | 6/2007 |
| JP | 2008-504319 A | 2/2008 |
| JP | 2008-179601 A | 8/2008 |
| WO | WO 02/02133 A2 | 1/2002 |
| WO | WO 02/46211 A2 | 6/2002 |
| WO | 03/091274 A2 | 11/2003 |
| WO | WO 2005/063196 A1 | 7/2005 |
| WO | WO 2006/000350 A2 | 1/2006 |
| WO | WO 2006000350 A2 * | 1/2006 |
| WO | WO 2006/095764 A1 | 9/2006 |
| WO | WO 2006/101187 A1 | 9/2006 |
| WO | WO 2006/137513 A1 | 12/2006 |

(Continued)

OTHER PUBLICATIONS

The Free Medical dictionary, definition of aging http://medical-dictionary.thefreedictionary.com/aging lastvisited Mar. 22, 2013.*
Extended European Search Report, dated Nov. 29, 2012, for European Application No. 09833435.2
Fisher et al., "Mechanisms of Photoaging and Chronological Skin Aging", Arch Dermatol., Nov. 2002; vol. 138, pp. 1462-1470.
Gomez-Ruiz, J.A., et al., "Sensory and Mass Spectrometric Analysis of the Peptidic Fraction Lower Than One Thousand Daltons in Manchego Cheese", Journal of Dairy Science, Nov. 2007, vol. 90, No. 11, pp. 4966-4973.

(Continued)

*Primary Examiner* — James H Alstrum Acevedo
*Assistant Examiner* — Jeanette Lieb
(74) *Attorney, Agent, or Firm* — Birch, Stewart, Kolasch & Birch, LLP

(57) ABSTRACT

The present invention provides a peptide and a composition which are suitable for oral ingestion, and which have a skin aging-inhibiting activity, a collagen-production promoting activity, an epidermal turnover promoting activity, and a cutaneous cell-proliferating effect. The present invention also provides a medicament and a functional food which have a skin aging-inhibiting activity, a collagen-production promoting activity, and a cutaneous cell-proliferation promoting activity. The present invention provides a composition including at least one peptide of Asn-lle-Pro-Pro-Leu, lle-Pro-Pro-Leu, lle-Pro-Pro, Pro-Val-Val-Val-Pro-Pro, Val-Pro-Pro-Phe, Val-Pro-Pro, Phe-Pro-Pro-Gln, and Leu-Pro-Pro-Thr.

2 Claims, 1 Drawing Sheet

(56) References Cited

FOREIGN PATENT DOCUMENTS

WO WO 2007/148803 A1 12/2007
WO WO 2010/024204 A1 3/2010

OTHER PUBLICATIONS

International Search Report PCT/JP2009/070912 dated Feb. 9, 2010.
Kafi et al., "Improvement of Naturally Aged Skin With Vitamin A (Retinol)", Arch Dermatol., May 2007, vol. 143, 5, pp. 606-612.
Kajimoto et al., "Safety evaluation of excessive intake of tablet containing "lactotripeptides (VPP, IPP)" in healthy subjects", Mar. 31, 2002, vol. 4, No. 4, pp. 37-46.
Kambayashi et al., "Epidermal changes caused by chronic low-dose UV irradiation induce wrinkle formation in hairless mouse", J. Dermatol. Sci. 27 Suppl. 1, 2001, pp. S19-S25.
Masuyama, "Effects of *Lactobacillus helveticus* Fermented Milk on Skin", Fragrance Journal, Oct. 15, 2005, vol. 33, No. 10, pp. 71-76.
Yamashita et al., Analysis of Drug Permeation Across Caco-2 Monolayer: Implication for Predicting In Vivo Drug Absorption, Pharm Res., Apr. 1997, vol. 14, No. 4, pp. 486-491.
Chinese Office Action, dated Feb. 22, 2013, for corresponding Chinese Application No. 200980156816.0.
Japanese Office Action issued in Japanese Patent Application No. 2010-542975 on Nov. 27, 2013.
Singh et al., "Isolation and identification of further peptides in the diafiltration retentate of the water-soluble fraction of Cheddar cheese", Journal of Dairy Research, col. 64 (1997) pp. 433-443.

\* cited by examiner

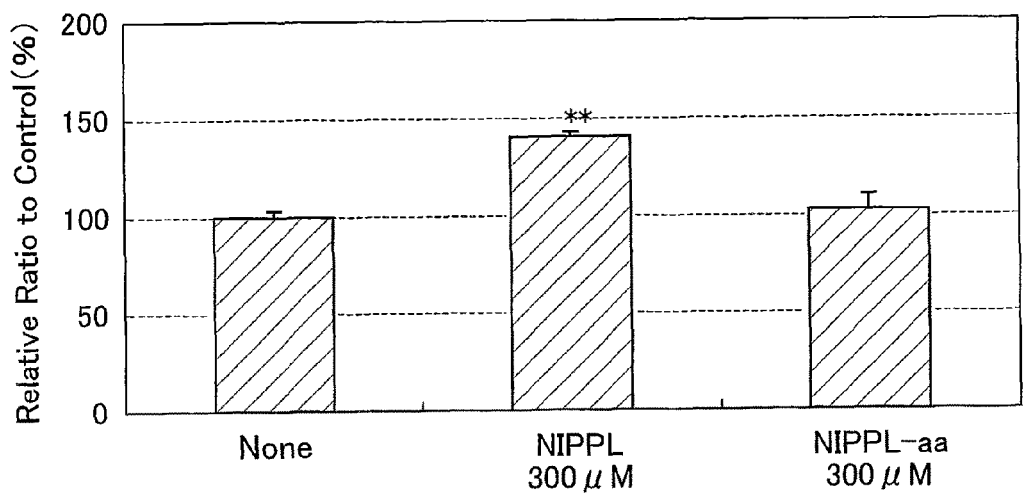
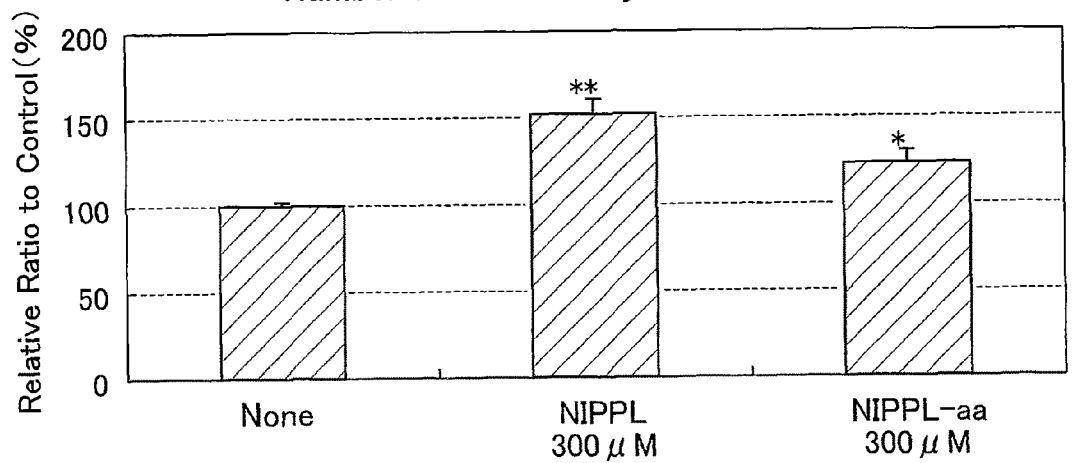

SEQUENCE LISTING

```
<160> NUMBER OF SEQ ID NOS: 10

<210> SEQ ID NO 1
<211> LENGTH: 3
<212> TYPE: PRT
<213> ORGANISM: Bos taurus

<400> SEQUENCE: 1

Ile Pro Pro
1

<210> SEQ ID NO 2
<211> LENGTH: 4
<212> TYPE: PRT
<213> ORGANISM: Bos taurus

<400> SEQUENCE: 2

Ile Pro Pro Leu
1

<210> SEQ ID NO 3
<211> LENGTH: 5
<212> TYPE: PRT
<213> ORGANISM: Bos taurus

<400> SEQUENCE: 3

Asn Ile Pro Pro Leu
1               5

<210> SEQ ID NO 4
<211> LENGTH: 3
<212> TYPE: PRT
<213> ORGANISM: Bos taurus
```

```
<400> SEQUENCE: 4

Val Pro Pro
1

<210> SEQ ID NO 5
<211> LENGTH: 4
<212> TYPE: PRT
<213> ORGANISM: Bos taurus

<400> SEQUENCE: 5

Val Pro Pro Phe
1

<210> SEQ ID NO 6
<211> LENGTH: 6
<212> TYPE: PRT
<213> ORGANISM: Bos taurus

<400> SEQUENCE: 6

Pro Val Val Val Pro Pro
1               5

<210> SEQ ID NO 7
<211> LENGTH: 4
<212> TYPE: PRT
<213> ORGANISM: Bos taurus

<400> SEQUENCE: 7

Phe Pro Pro Gln
1

<210> SEQ ID NO 8
<211> LENGTH: 4
<212> TYPE: PRT
<213> ORGANISM: Bos taurus

<400> SEQUENCE: 8

Asn Ile Pro Pro
1

<210> SEQ ID NO 9
<211> LENGTH: 4
<212> TYPE: PRT
<213> ORGANISM: Glycine max

<400> SEQUENCE: 9

Leu Glu His Ala
1

<210> SEQ ID NO 10
<211> LENGTH: 4
<212> TYPE: PRT
<213> ORGANISM: Bos taurus

<400> SEQUENCE: 10

Leu Pro Pro Thr
1
```

SKIN AGING-INHIBITING PEPTIDE

CROSS REFERENCE TO RELATED APPLICATIONS

This application is a Continuation of PCT International Application No. PCT/JP2009/070912 filed on Dec. 15, 2009, which claims priority under 35 U.S.C. 119(a) to Patent Application No. 2008-318334 filed in JAPAN, on Dec. 15, 2008, all of which are hereby expressly incorporated by reference into the present application.

FIELD OF THE INVENTION

The present invention relates to a peptide and a composition which have activities of preventing skin aging. More specifically, the present invention relates to a peptide and a composition which have a skin aging-inhibiting activity, a collagen-production promoting activity, an epidermal turn-over promoting activity (epidermal cell activating activity), and a cutaneous cell-proliferation promoting activity.

BACKGROUND OF THE INVENTION

Skin ages together with chronological aging like other living tissues, and its aging is accelerated by exposure to ultraviolet radiation. Recent research revealed that chronological aging-induced skin aging and ultraviolet radiation-induced skin aging shared several important molecular biological aspects.

The skin includes, from the outer side, the corneal layer, the epidermal layer, the dermis layer, and the subcutaneous tissue. The epidermal layer is constantly replaced with new epidermal cells which are born in the deepest epidermal basal layer and migrate up in an outward direction (this is called a turnover of epidermal cells). Known as factors of skin aging are a decrease in turnover of epidermal cells constituting the epidermal layer, and a decrease in collagen that exist between fibroblast cells in the dermis layer (Arch Dermatol. 2002; 138: 1462-1470). Collagen is a main component of the dermis layer, and is involved in maintaining of skin elasticity. It has been known that the amount of collagen in skin is decreased by chronological aging and damage due to ultraviolet radiation; consequently, the skin elasticity is lowered, and wrinkle formation and skin aging are accelerated. It is also known that drying causes thickening of the corneal layer and the epidermal layer and the delay in peeling off of the corneal layer causes shallow wrinkle formation (J. Dermatol. Sci. 2001; 27 Suppl 1: S19-25). Spot and sagging of skin are also main symptoms of skin aging and wrinkle formation is a major element of the skin aging. Accordingly, various methods have been conventionally taken for the prevention of such wrinkling, which includes, for example, a method of promoting synthesis of collagen fibers that support the skin structure and preventing a decrease in the collagen fibers. Moreover, promoting regeneration of the corneal layer and epidermal cells which is involved in maintaining moisture and barrier function of skin, i.e., promoting replacement of the epidermal layer and the corneal layer (epidermal turnover) (epidermal cell activation), is also thought as an effective wrinkle prevention method.

At present, generally widespread means for preventing wrinkles include components that provide moisture to skin, and cosmetics for external application in which a component for maintaining the elasticity is blended. Such cosmetics contain, for example, mucopolysaccharides such as hyaluronic acid or chondroitin sulfate, collagen, vitamins, amino acids, ceramides, or the like.

Recently, also developed are health and beauty foods which are considered to be good for skin. The examples includes: a collagen production promoting agent including an enzyme-hydrolyzed product of lactoferrin or an enzyme-hydrolyzed product of lactoperoxidase (JP-A 2004-331564, JP-A 2004-331565); a health and beauty food (JP-A 2006-143671) characterized by including mucopolysaccharides; and the like.

As low-molecular-weight compounds for promoting production of collagen, vitamins A such as retinoic acid and its derivative retinol are known (Arch Dermatol. 2007 May; 143(5): 606-12). Furthermore, there is a collagen-production promoting technique utilizing a peptide or an amino acid as a highly safe low-molecular-weight compound. For example, developed are a collagen-production promoting composition containing as an active ingredient peptides which is a collagen hydrolysate with collagenase (JP-A 2007-91637), and Leu-Glu-His-Ala derived from a soy protein or the like (JP-A 2007-145795). Moreover, also known is a beauty food in which three amino acids, L-proline, L-alanine and L-glycine, are blended at a ratio close to that in human skin collagen (JP-A 2001-224334).

Still furthermore, WO2006/000350 describes a milk protein hydrolysate containing a peptide of which terminal is proline, which has a cosmetic effect. This document describes that a cosmetic including a high content of peptides having prolines at the carboxyl terminals is effective. However, active ingredients are not specified, and absorption in the intestinal tract at the time of oral ingestion is not mentioned at all.

On the other hand, it has been presented that beauty effects such as suppressed ultraviolet-radiation sensitivity of skin, epidermal cell-differentiation promotion, and moisturization are observed in fermentation metabolites, such as fermented milk and whey, produced by a lactic acid bacterium (WO2006/095764, WO2006/137513, JP-A 2005-206578).

Furthermore, as a method for examining the absorption of drugs, peptides and the like, in the intestinal tract, an in vitro test system is known which uses permeability through a cell layer of Caco-2 cells which are epithelial cells derived from human colon cancer. The drug permeability test system using a monolayer cell culture of Caco-2 cells is known to be useful in predicting and evaluating in vivo drug absorption (Pharm Res. 1997 April; 14(4): 486-91).

SUMMARY OF THE INVENTION

To prevent and improve skin aging with wrinkling being the main symptom, increasing the amount of collagen in the dermis and promoting epidermal turnover are considered to be particularly effective. For this reason, it is desired to develop an active ingredient which has a noticeable collagen-production promoting ability on a fibroblast and an epidermal cell activating ability contributing to promotion of epidermal turnover, and which is particularly suitable for use in forms of food and beverage.

Even in a case of a peptide having an activity of promoting collagen production and an activity of promoting cutaneous cell-proliferation, if such a peptide is hard to absorb through the intestinal tract or readily hydrolyzed in the digestive tract, the peptide would have difficulties in exhibiting the collagen-production promoting activity and the cutaneous cell-proliferating activity when orally taken.

Accordingly, one object of the present invention is to provide a peptide and a composition which are suitable for oral ingestion, and which have an activity of inhibiting skin aging, an activity of promoting collagen production, an activity of promoting epidermal turnover, and an activity of promoting cutaneous cell-proliferation. Furthermore, the present invention provides a medicament and a functional food which have an activity of inhibiting skin aging, an activity of promoting collagen production, and an activity of promoting cutaneous cell-proliferation.

Moreover, the present invention provides a novel beauty food which is not readily hydrolyzed by an enzyme in a digestive tract, and which has an excellent absorption in an intestinal tract and further has skin aging-preventing and improving functions. Additionally, the present invention provides a novel beauty food having a collagen-production promoting activity, an epidermal turnover promoting activity, and a cutaneous cell-proliferation promoting activity.

The present invention is a collagen-production promoting composition, an epidermal turnover promoting composition, a cutaneous cell-proliferation promoting composition, or a skin-aging inhibiting composition, which are suitable for oral ingestion, and which include as an active ingredient at least one peptide of the following i) to viii) or a salt thereof:
i) Asn-Ile-Pro-Pro-Leu,
ii) Ile-Pro-Pro,
iii) Ile-Pro-Pro-Leu,
iv) Val-Pro-Pro,
v) Val-Pro-Pro-Phe,
iv) Pro-Val-Val-Val-Pro-Pro,
vii) Phe-Pro-Pro-Gln, and
viii) Leu-Pro-Pro-Thr.

Particularly, the present invention is a collagen-production promoting composition, an epidermal cell turnover promoting (epidermal cell activating) composition, a cutaneous cell-proliferation promoting composition, or skin-aging inhibiting composition for oral ingestion, which include as an active ingredient at least one peptide of the above i) to viii) or a salt thereof:

Furthermore, the present invention also provides a medicament or a functional food, particularly a beauty food, which include the peptide of i) to viii) or the salt thereof, or the composition.

The composition of the present invention is particularly suitable for oral ingestion by human.

The collagen-production promoting activity of the present invention is particularly remarkable on a fibroblast.

As used in the specification the single-letter code and the three-letter code for amino acids are in accordance with standard notation which is well known to persons skilled in the art.

BRIEF DESCRIPTION OF THE DRAWINGS

FIG. 1 shows the effect of a peptide Asn-Ile-Pro-Pro-Leu on collagen production and cell proliferation of fibroblasts (Example 2). FIG. 1A shows the amount of collagen produced at day 7 in culturing fibroblasts in the presence or absence of Asn-Ile-Pro-Pro-Leu. The vertical axis indicates an average value±mean error (%) of relative values assuming the amount of collagen produced with no added peptide as 100. NIPPL: peptide Asn-Ile-Pro-Pro-Leu, NIPPL-aa: a mixture of amino acids, Asn, Ile, Pro, and Leu, which are the constituent amino acids of Asn-Ile-Pro-Pro-Leu. $**$: P<0.01, $*$: P<0.05 (SNK test. No peptide was added for the Control). FIG. 1B shows the number of cells obtained at day 7 in culturing fibroblasts in the presence or absence of the Asn-Ile-Pro-Pro-Leu. The vertical axis indicates an average value±mean error (%) of relative values assuming the number of cells obtained with no added peptide as 100. NIPPL: peptide Asn-Ile-Pro-Pro-Leu, NIPPL-aa: a mixture of amino acids, Asn, Ile, Pro, and Leu, which are the constituent amino acids of Asn-Ile-Pro-Pro-Leu. $**$: P<0.01, $*$: P<0.05 (SNK test. No peptide was added for the Control.)

DESCRIPTION OF THE PREFERRED EMBODIMENTS

Collagen is the main component of dermis layer, and is involved in maintaining of skin elasticity. It is known that the amount of collagen in skin is decreased by chronological aging and damage due to ultraviolet radiation, consequently lowering the skin elasticity and progressing wrinkle formation and skin aging. It is also known that drying causes thickening of the corneal layer and the epidermal layer, and that the delay in peeling off of the corneal layer causes shallow wrinkle formation.

As described above, there are known cosmetics for external application in which a naturally-occurring polymer compound such as hyaluronic acid, chondroitin sulfate, or the like, is blended. However, since these mucopolysaccharides and collagen are high-molecular compounds, even when applied to a skin as an external applicant, these substances are hard to be absorbed into the skin. Furthermore, there are problems such as a residual gelatin odor derived from the raw material animals thereof. In addition, substances such as ceramides having a moisturizing effect merely improve the corneous state of the epidermis. Moreover, since a moisturizer for external application is to be applied to the skin, the users thereof may feel uncomfortable or unpleasant sensations in some cases. As for health and beauty foods, use of naturally-occurring components tends to be preferred from the standpoint of safety, and thus acceptable for the consumer. However, when orally administered, polymer compounds such as mucopolysaccharides are hardly digested and absorbed. Accordingly, their effects are not necessarily satisfactory.

It has been described that vitamin A such as retinoic acid and its derivative retinol are known to cause skin irritation. When externally applied, Vitamin A may cause inflammation in some cases. Moreover, it is pointed out that, when a large amount of vitamin A is ingested, it will accumulate in the liver and possibly causes liver damages.

Beauty foods in which amino acids such as L-proline, L-alanine, L-glycine are blended are known. These amino acids are glycogenic amino acids, a part or entire carbon skeletons thereof, after deamination or transamination, will enter the citric acid cycle, then participate in gluconeogenesis, and will be converted into glucose or glycogen (Seikagaku Jiten, second edition: p. 906, left column). For this reason, the effect caused by oral ingestion is believed to be small. To obtain a sufficient effect, the dose needs to be large, or such a beauty food needs to be used together with other components.

To prevent and improve skin aging such as wrinkling or to increase collagen production in this manner, various components and compositions have been developed. However, development has not been made yet on a skin-aging preventing technique which exhibits an excellent biological absorption and sufficient effects with a limited dose, which can be readily used in the form of a beauty food or the like and regardless of the gender, which also has such safety that allows uses in both external application and internal application, and which is continuously usable.

Beauty foods using particular peptides are known in prior art as described above, but it cannot be said that such foods are sufficiently utilized. This may be because the efficiency of biological absorption of these peptides has not been investigated. For a peptide orally taken to be incorporated into the body, the peptide has to be absorbed through the intestinal tract. Additionally, substances thus taken will be subjected to a digestive enzyme in the gastrointestinal tract. Thus, even when a useful, physiologically active peptide is found, the effectiveness of the peptide cannot be expected, if the peptide is readily hydrolyzed. Accordingly, in finding an active ingredient for oral ingestion, it is important to evaluate the absorption of a candidate substance in the intestinal tract and the degradability by a digestive enzyme.

As a method for determining the absorption of drugs, peptides, and the like in the intestinal tract, an in vitro test system is known which utilizes permeability through a layer of Caco-2 cells which are epithelial cells derived from human colon cancer. The drug permeability test system using a monolayer cell culture of Caco-2 cells is known to be useful in predicting and evaluation in vivo drug absorption (Pharm Res. 1997 April; 14(4): 486-91). This in vitro test system using the Caco-2 cells may be also used for screening the peptide which is an active ingredient of the present invention.

The present inventors have already reported that the beauty effects such as suppressed ultraviolet-radiation sensitivity of skin, epidermal cell-differentiation promotion, and moisturization are obtained through oral ingestion of fermented milk (WO2006/095764 WO2006/137513, JP-A 2005-206578), as described above. The present inventors further have found in fermented milk a peptide which is not readily hydrolyzed by enzymes in the digestive tract, has a permeability through epithelial cells in the intestinal tract, and further has a collagen-production promoting activity and/or an epidermal turnover promoting activity and/or an activity of promoting proliferation of epidermal cells. The inventors have revealed that the peptide therein is a peptide having an amino acid sequence of Asn-Ile-Pro-Pro-Leu (NIPPL), Ile-Pro-Pro (IPP), Ile-Pro-Pro-Leu (IPPL), Val-Pro-Pro (VPP), Val-Pro-Pro-Phe (VPPF), Pro-Val-Val-Val-Pro-Pro (PVVVPP), Phe-Pro-Pro-Gln (FPPQ), or Leu-Pro-Pro-Thr (LPPT), or a salt thereof.

Any of these peptides have a collagen-production promoting activity and/or an epidermal turnover promoting activity and/or an epidermal cell-proliferation promoting activity, and shows sufficient effects against skin aging. Particularly Asn-Ile-Pro-Pro-Leu has higher effects as compared with the other peptides in terms of collagen-producing ability and cell proliferation rate and a particularly high effect can be expected on prevention skin aging.

Any of the peptides, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, and Leu-Pro-Pro-Thr, may be an organochemically synthesized peptide or may be a naturally-occurring peptide. To synthesize these peptides organochemically, conventional methods such as a solid-phase method (Boc method, Fmoc method) and a liquid-phase method may be used. For example, the peptide may be synthesized by using an automated peptide synthesizer such as a peptide synthesizer (PSSM-8 system) manufactured by Shimadzu Corporation, for example. For the reaction conditions and the like for the peptide synthesis, synthesis method to be selected as well as appropriate reaction conditions and the like can be set up based on the technical common knowledge of persons skilled in the art. Methods for purifying the peptide thus chemically synthesized are also well known to those skilled in the art.

As used in the present specification, when these peptides are referred to, the "peptide" includes a salt thereof except for cases where particularly specified otherwise and where it is apparent that the salt is excluded from the context. Such a salt includes salts that may be present under a physiological condition such as a sodium salt and a potassium salt. Moreover, the composition of the present invention may include a free amino acid in addition to the peptides, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, and Leu-Pro-Pro-Thr, which are the active ingredients of the composition of the present invention.

The characteristics of peptide of the present invention (i.e. not being readily hydrolyzed by an enzyme in the digestive tract, and being excellent in permeability and absorption in the intestinal tract, furthermore having an activity of promoting collagen production and/or an activity of promoting epidermal turnover and/or an activity of promoting proliferation of epidermal cells, and the like) have not been known at all so far.

A collagen-production promoting composition, an epidermal turnover promoting (activating epidermal cells) composition, or a cutaneous cell-proliferation promoting composition of the present invention includes as an active ingredient the peptide having an amino acid sequence of Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, or Leu-Pro-Pro-Thr, or salt thereof. A "skin-aging inhibiting composition" as used in the present invention is a composition having an activity to suppress and stop the progress of wrinkle formation, having an activity to improve wrinkling, or having an effect to prevent wrinkling.

A daily administration amount or ingestion amount, for human, of the composition of the present invention includes generally about 10 µg to about 10 g, preferably about 1 mg to about 5 g, and more preferably about 3 mg to about 1 g of the peptide, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, or Leu-Pro-Pro-Thr and the composition may be also administered or taken separately several times a day.

In another embodiment of the present invention, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, or Leu-Pro-Pro-Thr may be derived from a fermented product obtained by fermenting a raw material containing a milk protein (for example, cow milk, horse milk, goat milk or sheep milk, their skimmed milk, or the like) with a bacterium belonging to a species of *Lactobacillus helveticus*. The content of the raw material, milk protein, for fermentation is not particularly limited, but is preferably 1 to 19 weight % in general.

An example of the bacterium belonging to a species of *Lactobacillus helveticus* is *Lactobacillus helveticus* CM4 strain (the National Institute of Bioscience and Human-Technology, Agency of Industrial Science and Technology in the Ministry of International Trade and Industry, 1-1-3, Higashi, Tsukuba, Ibaraki, postal code 305, Japan (currently, International Patent Organism Depositary, Advanced Industrial Science and Technology, Tsukuba, Central 6, 1-1-1, Higashi, Tsukuba, Ibaraki, postal code 305-8566, Japan), Deposit No. FERM BP-6060, deposited on Aug. 15, 1997) (hereinafter, simply referred to as a CM4 strain). When the peptide Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, or Leu-Pro-Pro-Thr is prepared by fermenting a raw material including a milk protein with a bacterium belonging to a species of *Lactobacillus helveticus* such as CM4 strain, the content of these peptides will be preferably 0.1 mg or more, and more preferably 1 mg or more, per 100 g of the fermented product.

This fermented product presumably contains the peptide Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, or Leu-Pro-Pro-Thr. This fermented product may be further digested with one or more enzymes localized in digestive tract, for example, pepsin and/or pancreatin. For example, the pepsin digestion can be carried out under the conditions of 37° C. and pH 2.0 for 2 hours, and the pancreatin digestion can be carried out under the conditions of 37° C. and pH 7.0 for 2 hours. The fermented product may be digested with any one of these enzymes, or with at least one of such digestive enzymes. For example, the aforementioned fermented product may be subjected to the pepsin digestion followed by the pancreatin digestion. For the hydrolysis with these digestive tract enzymes, the digestive tract enzyme to be used, the reaction liquid, and the reaction conditions such as enzyme treatment period and pH may be altered as appropriate.

Peptide in these fermented products or digestive enzyme-treated products may be tested for permeability through epithelium intestinal tract by a membrane permeation test with a cultured monolayer of Caco-2 cells, an everted sac method (J. Physiol. 123, 116-125, 1954), and the like. After the permeability of a peptide through epithelium intestinal tract is confirmed, the peptide may be purified by various methods, and the amino acid sequence thereof may be determined. For example, the peptide component may be concentrated by solid phase extraction (SepPak tC18, Waters), and then analyzed by using a high-performance liquid chromatograph tandem mass spectrometer (LCMS-IT-TOF, Shimadzu Corporation). Subsequently, based on information obtained from MS/MS measurement, de novo sequencing may be performed, and thus the amino acid sequence of the permeated peptide may be determined.

The activity of these peptides for promoting collagen production and promoting proliferation on fibroblasts may be confirmed as follows. Normal human dermal fibroblasts such as NHDF-NB are seeded at an appropriate density in 100 µL of an appropriate culture medium, for example, a concentration of $1.0 \times 10^4$ cells/ml, into each well of a 96-well plate, and the cells are cultured under humidified conditions at 37° C. and 5% $CO_2$ for 3 days. Subsequently, test samples dissolved in 100 µL of an appropriate buffer, for example, PBS, are added at various concentrations to the culture medium followed by culturing. After culturing them for 2 to 7 days, the culture medium is collected, and the concentration of type I collagen secreted into the culture medium is quantified by a method such as enzyme-linked immunosorbent assay to confirm the collagen-production promoting activity of the peptide on fibroblasts. Similarly, normal human dermal fibroblasts such as NHDF-NB are cultured in the presence of the peptide for a certain period, for example, 7 days, to confirm the cell-proliferation promoting activity of the peptide on fibroblasts by counting the number of cells. For both of amount of the produced collagen and the number of cells, the quantification may be carried out using as a control a cell culture without added peptide.

In still another embodiment of the present invention, the peptide Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln, or Leu-Pro-Pro-Thr may be derived from a hydrolysate of animal milk casein such as casein of cow milk, horse milk, goat milk, sheep milk, or the like, or from a concentrate of the hydrolysate. Moreover, the peptide may be derived from a fermented product obtained by fermenting a food raw material containing animal milk casein with *Aspergillus* or a bacterium such as a lactic acid bacterium, for example, lactic acid bacterium CM4 strain. When such animal milk casein is hydrolyzed or fermented, the casein concentration is not particularly limited, but generally 1 to 19 weight % is preferable. When commercially-available enzymes are used, optimal conditions may be generally indicated. However, conditions, for example, the amount of enzyme to be used, reaction period, and the like can be altered as appropriate so as to obtain the casein hydrolysate in accordance with the enzymes to be used.

If necessary, in a similar manner to that described for the fermented product with *Lactobacillus helveticus*, the functions of the peptide which is the active ingredient of the present invention may be confirmed by isolating (or without isolating) the peptide from the hydrolysate or concentrate thereof.

The administration or ingestion period of the composition of the present invention may be adjusted variously in consideration of a subject for administration or ingestion, and so forth, for example, the age of that person, and environment for skin aging of that subject. Generally, by ingesting the composition for at least 1 day, preferably 7 days or more, the long-lasting effect is expected. The mode of administration or ingestion composition of the present invention may be external application to the skin or oral ingestion, but preferably, oral ingestion, due to the favorable intestinal tract absorption thereof. When the composition of the present invention is used in the form of a medicament, the composition can be in a dosage form for oral administration. Examples thereof include a tablet, a pill, a hard capsule, a soft capsule, a micro capsule, a powder, a granule, a solution, and the like. When the composition is produced as a medicament, for example, pharmaceutically acceptable carrier, adjuvant, excipient, form-aiding agent, antiseptic, stabilizer, binder, pH regulator, buffer, thickener, gelling agent, preservative, antioxidant, or the like can be used appropriately as needed to produce the medicament in the unit dose form required for generally-approved drug administration.

The composition of the present invention can also be used as materials for a food and a beverage. For example, the composition of the present invention or the peptide which is the active ingredient of the composition of the present invention can be made into a functional food such as a food for specified health use having a skin aging-inhibiting activity and efficacy such as wrinkle prevention. From the standpoint that such a food, for example, a functional food, is taken routinely, continuously, or intermittently for a long period of time, the ingestion amount of Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln or Leu-Pro-Pro-Thr, which are the active ingredients, is generally about 10 µg to about 10 g, preferably about 1 mg to about 5 g, and further preferably about 3 mg to about 1 g per day for human to obtain such efficacy. The amount is based on the amount of the peptide, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln or Leu-Pro-Pro-Thr, which are the active ingredients. Depending on the number of times of ingestion per day, the ingestion amount at one time with respect to a food, for example, a functional food, can be further reduced than the above-described amount.

The food, for example, the functional food including the composition of the present invention or the peptide, Asn-Ile-Pro-Pro-Leu, Ile-Pro-Pro-Leu, Ile-Pro-Pro, Pro-Val-Val-Val- Pro-Pro, Val-Pro-Pro-Phe, Val-Pro-Pro, Phe-Pro-Pro-Gln or Leu-Pro-Pro-Thr, which are the active ingredients of the composition can be produced by adding to various foods: a fermented product itself of a raw material containing a hydrolysate of an animal milk casein, a concentrate thereof, or a milk protein, obtained as described above; or the fermented product in a powder or granular form. Additionally, as needed, the dietary balance, flavor, and the like may be improved by adding products fermented with lactic acid bacteria other than *Lactobacillus helveticus*, other components used for food, for example, sugars, proteins, lipids, vitamins, minerals, flavoring agents, additives such as, for example, various carbohydrates, lipids, vitamins, minerals, sweeteners, perfuming agent, pigments, texture improvers, or mixtures thereof.

The food, for example, the functional food, of the present invention can be in any form of a solid, a gel, and a liquid. Examples thereof include fermented milk products such as lactic fermented beverages, various processed foods and beverages, dried powders, tablets, capsules, granules, and the like. Furthermore, the food can be various beverages, yogurts, fluid diets, jellies, candies, high-pressure preserved foods, lozenge confectioneries, cookies, castellas, breads, biscuits, chocolates, and the like.

When the functional food such as a food for specified health use having a skin aging-inhibiting activity and efficacy such as wrinkle prevention is made by using the peptide, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln or Leu-Pro-Pro-Thr, the content of the peptide, Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln or Leu-Pro-Pro-Thr, which are the active ingredients included, is 0.01% by weight to 50% by weight, preferably 0.1% by weight to 30% by weight, and further preferably 1% by weight to 10% by weight based on the final product, although these values may vary depending on the mode of addition and types of product.

The in vivo effects of the composition of the present invention and the peptide which is the active ingredient thereof may be confirmed as follows.

The preventive effect on wrinkle formation due to ultraviolet radiation may be tested by an oral ingestion test of the peptide using hairless mice. Specifically, 5-week old male hairless mice (8 mice in a group) are irradiated with UVB ultraviolet radiation three times per week over 3 weeks; in the first week at 90 mJ/cm$^2$, in the second week at 120 mJ/cm$^2$, and in the third week at 150 mJ/cm$^2$. Additionally, during the irradiation with the ultraviolet radiation over 3 weeks, the hairless mice in each group are allowed to take water or water containing each test peptide or a mixture of the test peptides ad libitum. Then, 24 days after the first ultraviolet radiation, wrinkles are visually evaluated. This evaluation may be scored into, for example, 7 grades (Table 1). The scoring of wrinkles may be set with reference to, for example, Photodermatol. Photoimmunol. Photomed 7, 153-158, 1990. By this evaluation test, an excellent preventive effect on wrinkle formation may be confirmed in the group which has taken water containing the peptide of the present invention or the mixture thereof.

TABLE 1

| Score for visual observation of wrinkles | |
|---|---|
| 0.0 | no skin groove is observed on the skin of the dorsal region |
| 0.5 | skin grooves are observed partially but conspicuously on the skin of the dorsal region |

TABLE 1-continued

| Score for visual observation of wrinkles | |
|---|---|
| 1.0 | skin grooves are observed throughout on the skin of the dorsal region |
| 1.5 | Among the skin grooves observed throughout on the skin of the dorsal region, skin grooves running horizontally are deeper than skin grooves running vertically |
| 2.0 | Among the skin grooves observed throughout on the skin of the dorsal region, skin groove running horizontally are much deeper than skin grooves running vertically |
| 2.5 | wrinkles are observed throughout on the skin of the dorsal region |
| 3.0 | deep wrinkles are observed throughout on the skin of the dorsal region |

The in vivo effect of the composition of the present invention or the peptide which is the active ingredient thereof may be confirmed by other evaluation methods such as a natural aging model where aged mice are used, a dry skin model where an organic solvent such as acetone is applied, or a rough skin model where irritation is caused by a surfactant such as an aqueous solution of sodium dodecyl sulfate.

The present invention will be more specifically described below by Examples, but the scope of the present invention is not limited to the Examples.

EXAMPLES

Example 1

Screening of Peptides that are Resistant to Hydrolysis but are Ready to be Absorbed 1) Preparation of Fermented Milk Reconstituted skimmed milk with a reconstitution ratio of 8.9% was inoculated with 3 to 5% of *Lactobacillus helveticus* CM4 strain starter, and fermented at 30 to 32° C. for 16 hours or longer. Thus, lactic acid bacterium-fermented milk was prepared.

2) Hydrolysis of Fermented Milk with Digestive Tract Enzyme

In considering the degradation of peptides with a digestive tract enzyme at the time of oral ingestion, hydrolyzation was carried out with a digestive tract enzyme. A digestive tract enzyme pepsin (Sigma) was used for the aforementioned fermented milk, and the reaction solution was reacted at pH 2 and 37° C. for 2 hours. Subsequently, the pH of the solution was adjusted to 7, and then a digestive tract enzyme pancreatin (Sigma) was used under the reaction conditions of 37° C. for 2 hours enzyme treatment of the fermented milk. After the enzyme treatment, the solution was heated at 95° C. to inactivate the enzymes. A powder of a degraded product from the fermented milk with the digestive tract enzymes was obtained By freeze-drying.

3) Permeation Test with Cultured Monolayer Membrane of Caco-2 Cells, and Screening of Peptides Caco-2 cells were obtained from the American Type Culture Collection. Cells with a passage number of 40 to 70 were used for the permeation test. The culture medium comprised Dulbecco's modified Eagle's medium (Sigma) supplemented with fetal bovine serum (10%, AGC TECHNO GLASS CO., LTD.), a non-essential amino acid solution (1%, Gibco), and penicillin-streptomycin (each 200 IU/ml, 200 µg/ml, Gibco). The Caco-2 cells were cultured under humidified conditions at 37° C. and 5% $CO_2$, and subcultured for every 4 to 5 days. For the permeation test, the cells were cultured on a membrane filter in a 12-transwell (Millipore). To a basal side 1.5 ml of the culture medium was added and 0.5 ml of culture medium was added to an apical side, and the cells were cultured for approximately 2 weeks. The enzymatic hydrolysate of the fermented milk was added to the apical side of the cultured Caco-2 cells. Peptides which were permeated to the basal side were collected. For comparison, the same test was performed on a digestive tract enzyme-degraded product of non-fermented reconstituted skimmed milk with a reconstitution ratio of 8.9%.

4) Amino Acid Sequence Analysis by LC/MS/MS, and Identification of Peptides

The peptides which were permeated to the basal solution were subjected to solid phase extraction (SepPak tC18, Waters) to thereby concentrate the peptide component and then the peptides were determine by using a high-performance liquid chromatograph tandem mass spectrometer (LCMS-IT-TOF, Shimadzu Corporation). PEAKS (Bioinformatics Solutions Inc) was used to analyze the data. Based on the information obtained from MS/MS, de novo sequencing was performed to determine the amino acid sequence of the permeated peptides. Comparison was made between the detected peptides and peptides contained in a digestive tract enzyme-hydrolyzed product of a milk protein. Thus, permeable peptides such as Asn-Ile-Pro-Pro-Leu, Ile-Pro-Pro, Ile-Pro-Pro-Leu, Val-Pro-Pro, Val-Pro-Pro-Phe, Pro-Val-Val-Val-Pro-Pro, Phe-Pro-Pro-Gln, Leu-Pro-Pro-Thr were identified, which can not be generated only through hydrolysis with the digestive tract enzymes such as pepsin and pancreatin, and which are therefore peculiar to fermented milk.

Example 2

Tests for Collagen-Production Promotion and Cell Proliferation in Fibroblast

Synthesis of the peptides Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln and Leu-Pro-Pro-Thr was entrusted to Scrum Inc. via solid-phase synthesis process using Fmoc method, and the peptides were purified by preparative HPLC (to 99% purity).

Normal human dermal fibroblasts (NHDF-NB: Kurabo Industries Ltd.) were seeded at a concentration of $1.0 \times 10^4$ cells/mL in 100 µL in each well of a 96-well plate, and cultured under humidified conditions at 37° C. and 5% $CO_2$ for 3 days. For the culture medium 100 µL of Medium 106S (Kurabo Industries Ltd.) supplemented with LSGS (Kurabo Industries Ltd.) at a concentration of 10 weight % was used for each well. Then, the medium was replaced with Dulbecco's modified Eagle's medium (DMEM: Sigma). Furthermore, test samples dissolved in 100 µL of PBS (Takara Bio Inc.) were added at the respective concentrations to the medium followed by further culturing. As a control the medium into which 100 µL of PBS without dissolved test sample was added was used. For the test for collagen-production promotion, after culturing the cells for 2 to 7 days, the culture medium was collected, and the concentration of type I collagen secreted into the culture medium was quantified by enzyme-linked immunosorbent assay (Procollagen type I c-peptide EIA Kit; Takara Bio Inc.). Based on the quantification result, the amount of collagen in the culture medium containing each of the test samples was calculated assuming the amount of type I collagen in the control culture medium as 100% (Table 2, FIG. 1(A)). Moreover, for the cell proliferation test, after culturing the cells for 7 days, the culture medium was discarded, and 100 µL of PBS was added, and then, the number of cells was counted using CellTiter-Glo (Promega KK). Based on the quantification result, the number of cells cultured in the culture medium containing each of the test samples was calculated and shown assuming the number of cells cultured in the control culture medium as 100% (FIG. 1(B)).

As a comparative example, a mixture of amino acids constituting Asn-Ile-Pro-Pro as well as Leu-Glu-His-Ala, and Asn-Ile-Pro-Pro-Leu was used, which were considered to have an activity of promoting collagen-production according to WO2006/000350 (DSM) and JP-A 2007-145795 (ROHTO Pharmaceutical Co., Ltd.).

Cell Proliferation Test in Epidermal Keratinocyte

Furthermore, normal human epidermal keratinocytes (NHEK-F: Kurabo Industries Ltd.) was seeded at a concentration of $1.0 \times 10^5$ cells/mL in 100 µL into each well of a 96-well plate, and cultured under humidified conditions at 37° C. and 5% $CO_2$ for 14 days. For the culture medium, 100 µL of Humedia-KB2 (Kurabo Industries Ltd.) supplemented with a proliferation additive (Kurabo Industries Ltd.) was used for each well. Then, test samples dissolved in 100 µL of PBS (Takara Bio Inc.) were added at the respective concentrations to the medium followed by culturing. A medium into which 100 µL of PBS without dissolved test sample was added was used as a control. After culturing for 7 days, the culture liquid was discarded, and 100 µL of PBS was added. Then, the number of cells was counted by using CellTiter-Glo (Promega KK). Based on the quantification result, the number of cells in the culture for each of the test samples was calculated and shown assuming the number of cells cultured in the control culture as 100% (Table 2).

As a comparative example, a mixture of amino acids constituting each of the peptides and Asn-Ile-Pro-Pro was used, which were considered to have an activity of promoting proliferation of epidermal cells according to WO2006/000350 (DSM).

It was revealed that any of Asn-Ile-Pro-Pro-Leu, Ile-Pro-Pro-Leu, Ile-Pro-Pro, Pro-Val-Val-Val-Pro-Pro, Val-Pro-Pro-Phe, Val-Pro-Pro, Phe-Pro-Pro-Gln and Leu-Pro-Pro-Thr had remarkable collagen-producing ability and cell-proliferation promoting activity, and showed sufficient effects against skin aging, and Asn-Ile-Pro-Pro-Leu had particularly higher effects than the other peptides in terms of collagen-producing ability and cell proliferation rate.

TABLE 2

Effects of various peptides on collagen production amount on fibroblasts and on cell proliferation rate on epidermal keratinocytes

| | Amount of collagen production (%) of skin fibroblasts | | Cell proliferation rate (%) |
| --- | --- | --- | --- |
| Peptide sequence | Cultured for 2 days | Cultured for 4 days | of epidermal keratinocytes |
| Asn-Ile-Pro-Pro-Leu | 132 ± 5 | 131 ± 5 | 121 ± 2 |
| Ile-Pro-Pro-Leu | 114 ± 4 | 108 ± 4 | 114 ± 2 |
| Ile-Pro-Pro | 118 ± 4 | 124 ± 4 | 119 ± 2 |
| Pro-Val-Val-Val-Pro-Pro | 120 ± 3 | 111 ± 5 | 114 ± 0 |
| Val-Pro-Pro-Phe | 105 ± 3 | 109 ± 3 | 114 ± 3 |
| Val-Pro-Pro | 112 ± 3 | 117 ± 4 | 111 ± 2 |
| Phe-Pro-Pro-Gln | 106 ± 3 | 109 ± 5 | 111 ± 0 |
| Leu-Pro-Pro-Thr | 108 ± 4 | 104 ± 5 | 108 ± 5 |
| Leu-Glu-His-Ala | 94 ± 4 | — | — |
| Asn-Ile-Pro-Pro | 123 ± 4 | 113 ± 6 | 115 ± 0 |
| Asn, Ile, Leu: 300 µM Pro: 600 µM | — | | 107 ± 4 |
| Ile: 300 µM Pro: 600 µM | — | | 107 ± 2 |
| Val: 300 µM Pro: 600 µM | — | | 107 ± 2 |

TABLE 2-continued

Effects of various peptides on collagen production amount on fibroblasts and on cell proliferation rate on epidermal keratinocytes

| Peptide sequence | Amount of collagen production (%) of skin fibroblasts | | Cell proliferation rate (%) of epidermal keratinocytes |
|---|---|---|---|
| | Cultured for 2 days | Cultured for 4 days | |
| Pro: 900 μM Val: 900 μM | — | | 105 ± 1 |
| Phe, Gln: 300 μM Pro: 600 μM | — | | 97 ± 2 |

\* Each value represents a mean value ± standard error of the mean value where the value obtained when no peptide was added is assumed as 100
\* The concentration of the sample added was 100 μM in the test for collagen-production promotion, and 300 μM in the test for epidermal cell proliferation.

The present invention provides a peptide and a composition which exhibits activities of prevent skin aging and deterioration of skin by oral ingestion. More specifically, the present invention provides a peptide and a composition which are suitable for oral ingestion, and which have an activity of inhibiting skin aging, an activity of promoting collagen-production, an activity of promoting epidermal turnover (activating epidermal cells), and an activity of proliferating cutaneous cells. The composition of the present invention is particularly suitable for oral ingestion by human.

Collagen is the main component of the dermis layer, and is involved in maintaining of skin elasticity. It is known that the amount of collagen in skin decreased by chronological aging and damage due to ultraviolet radiation; consequently the skin elasticity is lowered, and wrinkle formation and skin aging are progressed. It is also known that, although drying causes thickening of the corneal layer and the epidermal layer, the delay in peeling off of the corneal layer causes shallow wrinkle formation.

The peptide included in the composition of the present invention is not readily hydrolyzed by enzymes in the digestive tract and has an excellent absorption in the intestinal tract. Moreover, since the peptides are derived from fermented milk, they are also excellent in safety. Thus, according to the present invention it is possible to prevent such aging and deterioration of skin safely and easily.

References

1. JP-A 2004-331564
2. JP-A 2004-331565
3. JP-A 2006-143671
4. JP-A 2007-91637
5. JP-A 2007-145795
6. JP-A 2001-224334
7. WO2006/000350
8. WO2006/095764
9. WO2006/137513
10. JP-A 2005-206578
11. Arch Dermatol. 2002; 138: 1462-1470
12. J. Dermatol. Sci. 2001; 27 Suppl 1: S19-25
13. Arch Dermatol. 2007 May; 143(5): 606-12
14. Pharm Res. 1997 Apr; 14(4): 486-91

What is claimed is:

1. A method of treating the symptoms of skin aging, comprising:
   administering at least one peptide consisting of the following i) to vi) or a salt thereof to a subject with symptoms of skin aging to promote collagen production and/or epidermal cell proliferation:
   i) Asn-Ile-Pro-Pro-Leu (SEQ ID NO: 3),
   ii) Ile-Pro-Pro-Leu (SEQ ID NO: 2),
   iii) Val-Pro-Pro-Phe (SEQ ID NO: 5),
   iv) Pro-Val-Val-Val-Pro-Pro (SEQ ID NO: 6),
   v) Phe-Pro-Pro-Gln (SEQ ID NO: 7), and
   vi) Leu-Pro-Pro-Thr (SEQ ID NO: 10),
   wherein the symptoms of skin aging are selected from the group consisting of wrinkles, spots and sagging of skin.

2. A method of claim 1, wherein the at least one peptide is administered orally.

* * * * *